(12) United States Patent
McDonald

(10) Patent No.: US 7,063,084 B2
(45) Date of Patent: *Jun. 20, 2006

(54) OXYGEN DIFFUSER SUPPORT

(75) Inventor: Lee McDonald, Barrie (CA)

(73) Assignee: Soutmedic Incorporated, Barrie (CA)

( * ) Notice: Subject to any disclaimer, the term of this patent is extended or adjusted under 35 U.S.C. 154(b) by 122 days.

This patent is subject to a terminal disclaimer.

(21) Appl. No.: 10/757,339

(22) Filed: Jan. 14, 2004

(65) Prior Publication Data

US 2005/0150498 A1    Jul. 14, 2005

(51) Int. Cl.
*A62B 29/00* (2006.01)
(52) U.S. Cl. ............... 128/200.28; 128/207.17; 128/206.27; 128/206.28
(58) Field of Classification Search ......... 128/200.28, 128/201.24, 207.17, 207.18, 201.19, 200.27, 128/204.23, 200.18, 205.11, 205.25
See application file for complete search history.

(56) References Cited

FOREIGN PATENT DOCUMENTS

CA            93613         10/2001

OTHER PUBLICATIONS

U.S. Appl. No. 09/977,148, filed Oct. 12, 2001, McDonald.
U.S. Appl. No. 10/186,015, filed Jul. 1, 2002, McDonald.
U.S. Appl. No. 09/572,637, filed May 17, 2000, McDonald et al.
U.S. Appl. No. 09/659,503, filed Sep. 11, 2000, McDonald.
U.S. Appl. No. 29/131,646, filed Oct. 25, 2000, McDonald.
U.S. Appl. No. 29/141,424, filed May 4, 2001, McDonald et al.
U.S. Appl. No. 29/136,099, filed Jan. 24, 2001, McDonald et al.
U.S. Appl. No. 09/849,863, filed May 4, 2001, McDonald et al.

*Primary Examiner*—Henry Bennett
*Assistant Examiner*—Shumaya B. Ali
(74) *Attorney, Agent, or Firm*—Nikolai & Mersereau, P.A.

(57) ABSTRACT

A support for an oxygen diffuser for delivering a plume of oxygen-enriched air to a space in front of a patient's nose and mouth. The support comprises a means for holding a tube associated with the oxygen diffuser. This means is located at the vertex of front portions of rigid arms forming a v-shaped front of the support. A resilient front strap extends between rear portions of the arms. A resilient back strap extends between ends of the rear portions of the arms. In operation, the back strap is arranged so as to extend behind a user's head and is releasably adjustable to an operative length to seat the support securely on a user's head with a portion of the front of the user's face bearing against the front strap, so that, when so seated, the diffuser is held in a position spaced from but proximal to the patient's nose and mouth.

20 Claims, 4 Drawing Sheets

OXYGEN DIFFUSER SUPPORT

BACKGROUND OF THE INVENTION

The present invention relates to a support for securely holding in position on a patient's head an oxygen diffuser for delivery of a plume of oxygen-enriched air to a space in front of the patient's nose and mouth.

In recent years, an alternative system to conventional oxygen masks and nasal cannulas has been developed for delivery of oxygen to a patient, as described for example, in applicant's U.S. application Ser. Nos. 09/572,637 now U.S. Pat. No. 6,450,166 and U.S. application Ser. No. 09/659,503 now U.S. Pat. No. 6,595,207. Central to such system is an oxygen diffuser which comprises a body having a wall, the interior surface of which wall is generally of concave configuration and circumscribes a centrally positioned oxygen outlet so as to direct the flow of oxygen from the outlet generally towards a patient's nose and mouth. A baffle is seated over the oxygen outlet, the baffle being positioned and designed so as to generate turbulence in the oxygen stream and thereby assist in mixing of oxygen with ambient air. This avoids a direct flow of oxygen towards a patient's face. This diffuser produces a plume of oxygen-enriched air which is then be directed towards the nose and mouth area of a patient's face.

One of the challenges confronting widespread use of this new oxygen diffuser system has been to ensure that the diffuser is securely held in position proximal to, but spaced from, a user's nose and mouth. Use of a headband or ear support, as described and illustrated in applicant's co-pending U.S. application Ser. No. 09/572,637 is suitable for a patient that is fully cognitive and not agitated. However, such diffuser supports can easily be dislodged partially or completely, for example, by movement of a sleeping or agitated patient, restricting the practical applications of such a diffuser.

Alternative solutions for holding the diffuser in position on a patient's head have been described in applicant's co-pending U.S. application Ser. No. 09/977,148 which describes and illustrates a flexible attachment which secures to a portion of the diffuser and has adhesive for releasably attaching to a patient's chin or cheek and co-pending U.S. application Ser. No. 10/186,015 which describes and illustrates a diffuser attachment which has flexible wings for seating on both sides of a patient's nose or chin, and an elastic band which is secured to the wings so that the strap can extend around the patient's head, when in operation, to secure the wings in position.

These alternative constructions still present difficulties: adhesives can be difficult to apply, and unreliable, causing the diffuser to fall off, and painful to remove; the flexible wings do not provide an adequately comfortable and secure fit for the diffuser and can also be hard to place in position and remove from a patient.

It is thus an object of the present invention to provide a diffuser support which can be securely fitted and positioned on a patient and which will provide greater resistance against unintentional dislodgement during sleep or agitated behavior. It is a further object of the present invention to provide such a support which is relatively easy to place in position on, and remove from, a patient's head, and which will be relatively comfortable to wear.

SUMMARY OF THE INVENTION

In accordance with the present invention, there is provided a support for an oxygen diffuser for delivering a plume of oxygen-enriched air to a space in front of a patient's nose and mouth. The support comprises a means for holding a tube associated with the oxygen diffuser. This means is located at the vertex of front portions of arms forming a v-shaped front of the support. A resilient front strap extends between rear portions of the arms. A resilient back strap extends between ends of the rear portions of the arms. In operation, the back strap is arranged so as to extend behind a user's head and is releasably adjustable to an operative length to seat the support securely on a user's head with a portion of the front of the user's face bearing against the front strap, so that, when so seated, the diffuser is held in a position spaced from but proximal to the patient's nose and mouth.

In a one embodiment, this support further comprises one end of the back strap which is anchored to the corresponding arm, and another end of the back strap which is slidable and releasably securable within a keyway aperture in the end of the other arm, to permit adjustment of the operative length of the back strap.

In a further embodiment, this support further comprises a carbon dioxide sensor secured to but movably positionable on an arm of the brace. The sensor is positioned in spaced relationship with respect to the diffuser but positionable so as to be proximal to the patient's nose and mouth.

The support according to the present invention permits a comfortable yet secure placement of a diffuser of the type in question on a patient so that there is a minimized risk of unintended dislodgement of the diffuser from its position on the patient.

BRIEF DESCRIPTION OF THE DRAWINGS

These and other advantages of the invention will become apparent upon reading the following detailed description and upon referring to the drawings in which.

Figure 1:
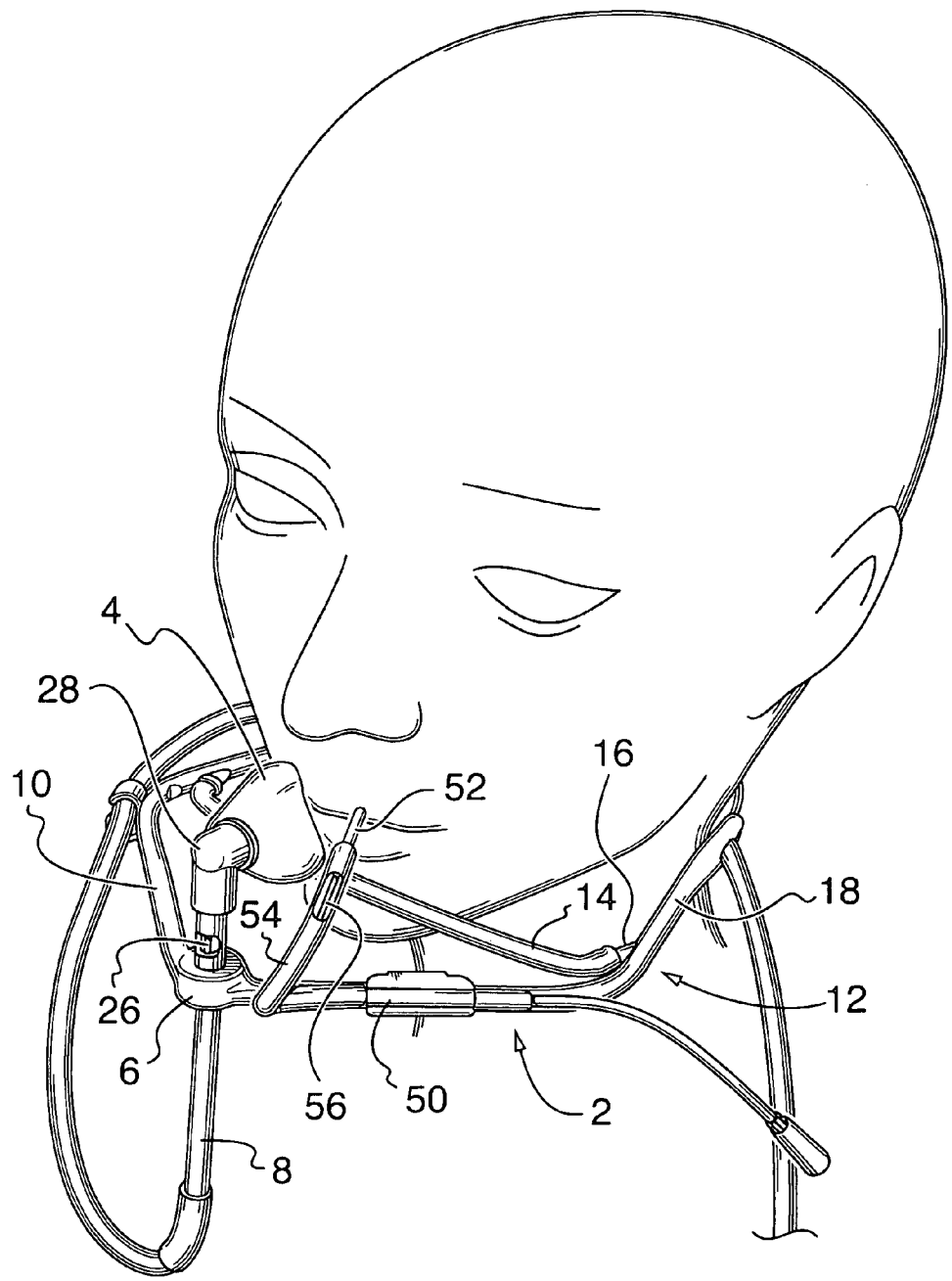
FIG. 1 is a perspective view of a support, in accordance with the present invention, mounted at the chin level on the head of a patient, the support as illustrated holding both a diffuser and a carbon dioxide monitor inlet.

While the invention will be described in conjunction with the illustrated embodiment, it will be understood that it is not intended to limit the invention to such embodiment. On the contrary, it is intended to cover all alternatives, modifications and equivalents as may be included within the spirit and scope of the invention as defined by the appended claims.

DETAILED DESCRIPTION OF THE INVENTION

In the following description, similar features in the drawings have been given similar reference numerals.

Turning to FIG. 1 there is illustrated a support 2 for an oxygen diffuser 4 for delivering a plume of oxygen-enriched air to a space in front of a patient's nose and mouth. The oxygen diffuser support comprises a sleeve 6 for securely holding tube 8 which delivers oxygen from an oxygen source (not illustrated) to diffuser 4. Sleeve 6 is located at the vertex of front portions 10 of arms 12, these portions and the sleeve forming a v-shaped front portion of support 2. A resilient front strap 14, preferably made of rubber tubing, extends between anchor pins 16 inwardly projecting at the front of rear portions 18 of arms 12. It is preferred that sleeve 6 and arms 12 be of integral construction and made, for example, of a suitable plastic material.

At the rear ends 20 of rear portions 18 of arms 12 (FIG. 2) is adjustably secured a resilient back strap 22. Again this strap is preferably of rubber tubing. One end of strap 22 is suitably anchored to one of the rear ends to a pin 23 or other anchoring means. The other end of strap 22 is slidable, and adjustably and releasably securable, in a keyhole slot 24 in the rear end of the other arm 12. Back strap 22 can thus be tightened, behind the neck (FIG. 1) or forehead (FIG. 4) of a patient, so that the support 4 is securely held with the front strap 14 resiliently bearing against the patient's chin (FIG. 1) or forehead (FIG. 4), the diffuser being generally positioned and oriented in the proper direction to bathe the patient's nose and mouth area with the plume of oxygen-enriched air from diffuser 4.

Figure 2:
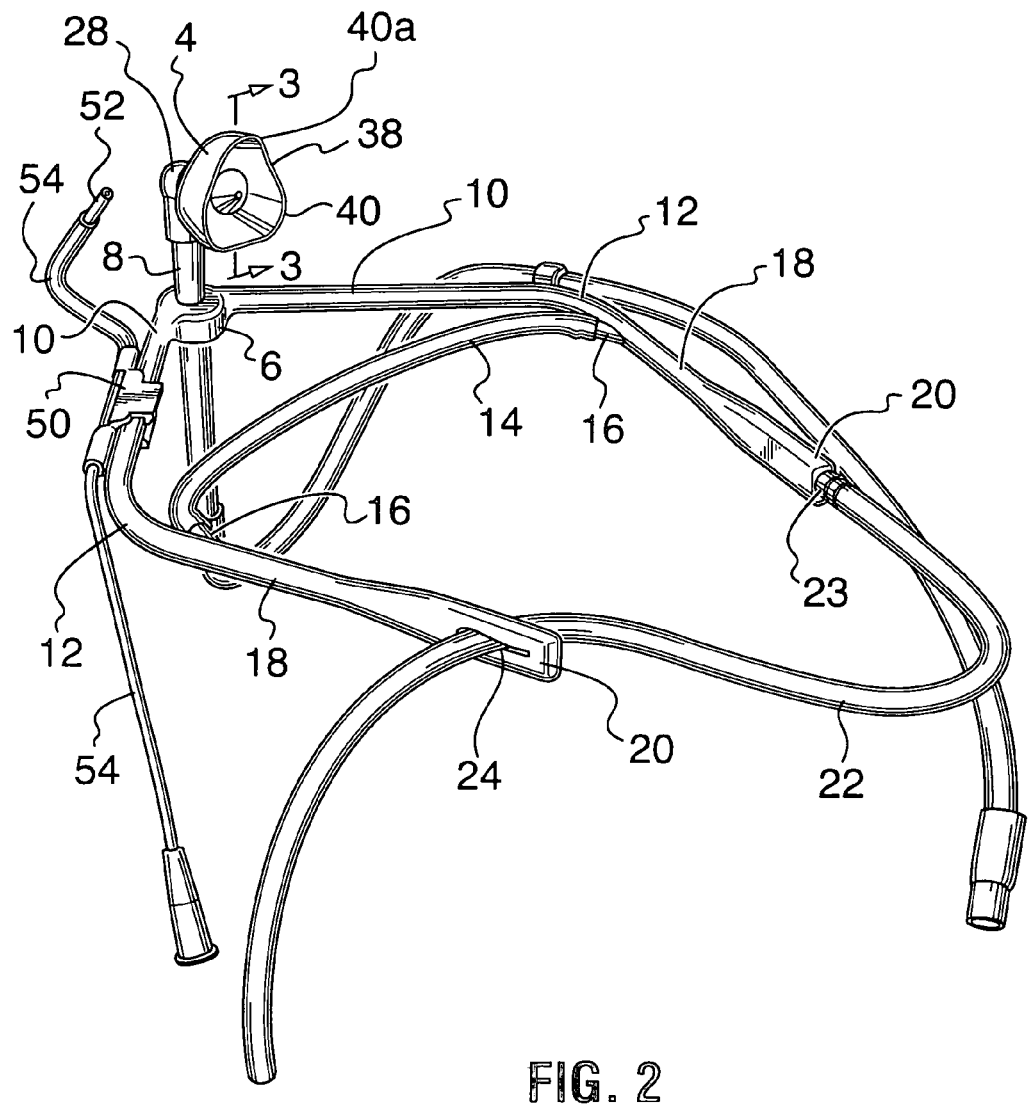
FIG. 2 is a perspective view of the device of FIG. 1, from the rear.

As can be seen in FIG. 2, diffuser 4 is associated with tube 8 for oxygen delivery. That tube is bendable to a particular shape and can maintain that shape. This feature is achieved by a fairly stiff, bendable wire 26 (FIG. 1) being embedded in the tube 8 during its manufacture. At one end of oxygen delivery tube 8 is a rigid elbow 28, provided with an oxygen delivery passageway 30 (FIG. 3), extending from one end of the elbow to the other. Oxygen delivery tube 8 communicates with that passageway at one end of the elbow. Oxygen diffuser 4 is rotatably connected to its other end as illustrated. This diffuser has a body 32 formed from a wall 34 of cup-shaped appearance, extending from a base 36 which circumscribes an oxygen outlet 38, which in turn communicates with the oxygen delivery passageway 30 of elbow 28. Wall 34 extends from that base upwardly and outwardly to an edge 38 of triangular peripheral contour (FIG. 1). The peripheral corners 40 of that edge are rounded, with one of the corners, 40a, intended to be the corner positionally related to the patient's nose, being raised with respect to the other corners and their proximal edge wall portions as illustrated, to facilitate the direction of oxygen towards a patient's nose and mouth. This construction, with protruding corner 40(a) and proximal edges of the wall 34 being positioned proximal to the patient's nose when in use, and the wider triangular portion at the bottom proximal to a patient's mouth, provides optimal oxygen delivery to a patient.

The avoidance of a direct flow of air from diffuser 4 onto a patient's face is achieved by a mushroom-shaped baffle 42 (FIG. 3) which is seated over oxygen outlet 38 to assist in the generation of turbulence in the flow of oxygen. Baffle 42 comprises a post 44 secured to and upwardly extending from a central portion of base 36 of diffuser 4 over oxygen outlet 38 of elbow 28. Post 44 extends upwardly to a cap 46 having outwardly flared edges, as illustrated, extending back towards oxygen outlet 38. This shaping of cap 46 impedes oxygen flow from the rear of the body 32 of diffuser 4, inducing a transmission of that flow from jet to turbulent flow. This particular shaping of baffle 42, and that of diffuser body 32, directly influences the mixing characteristics between pure oxygen stream and ambient air (containing approximately 21% oxygen by volume), and thus determines the oxygen content and shape of the plume of oxygen-enriched air delivered from the diffuser 4 to the surface of the patient's face.

Figure 3:
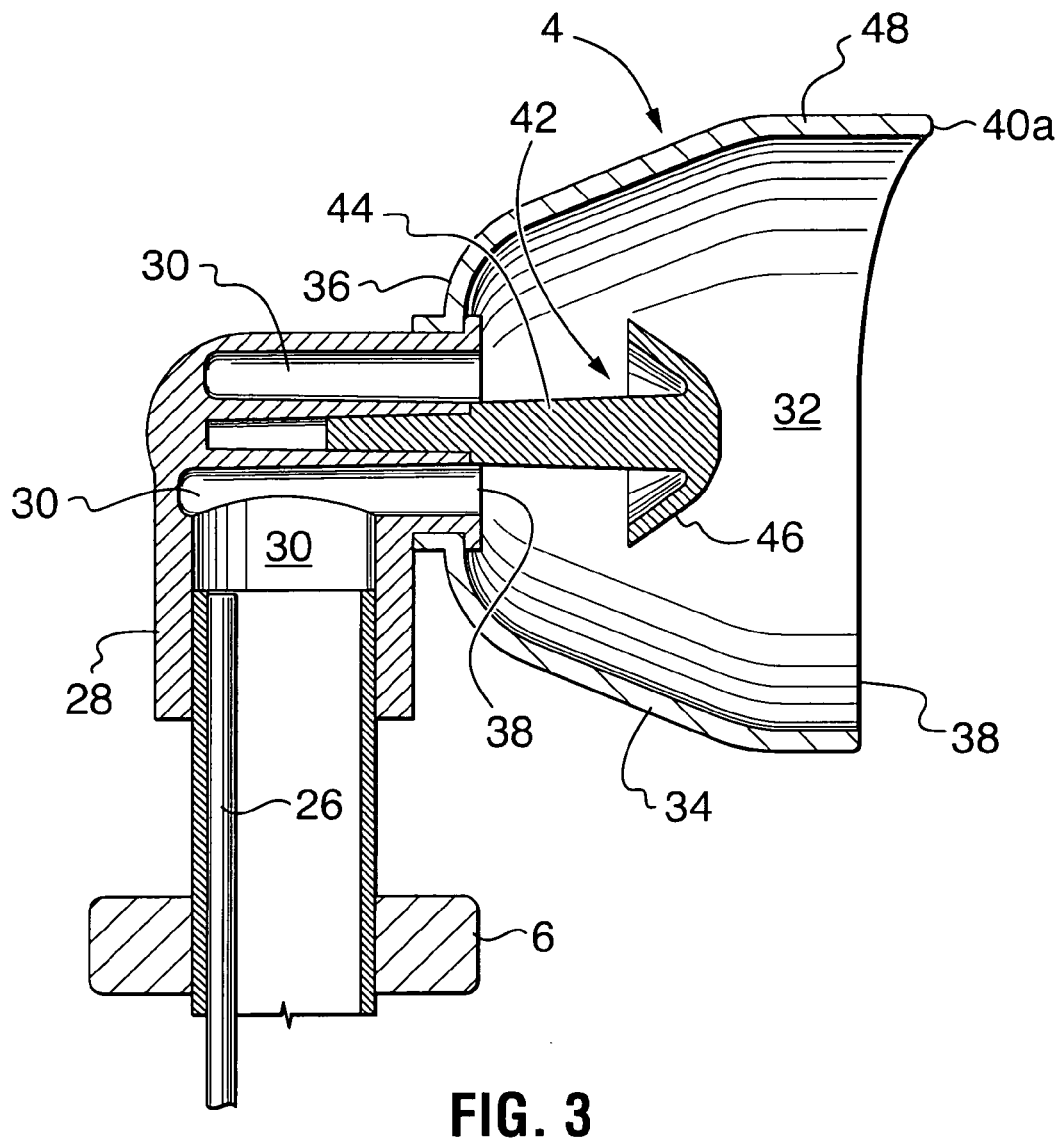
FIG. 3 is a side section view of a portion of the device of FIGS. 1 and 2, taken along line 3—3 of FIG. 2.
Figure 4:
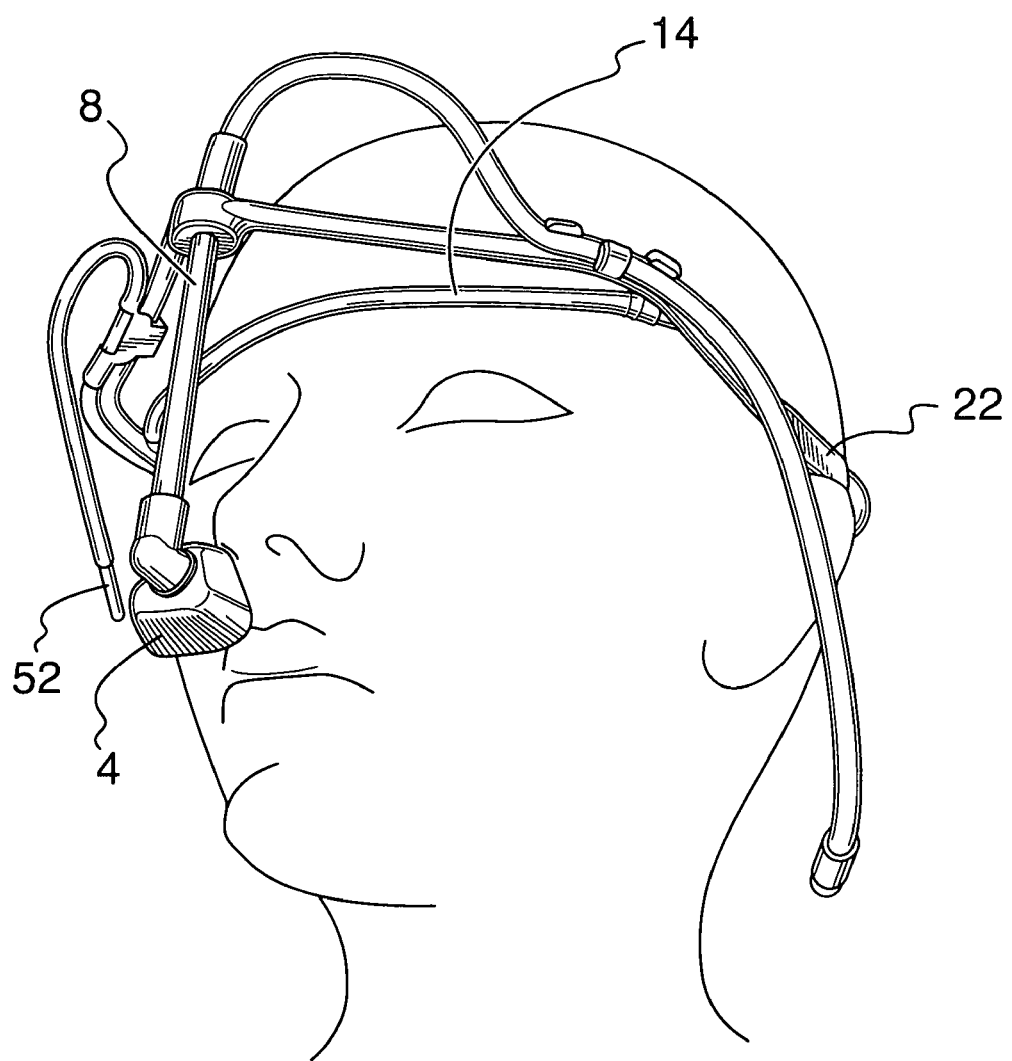
FIG. 4 is a perspective view of the device of FIG. 1, mounted at the forehead level on the head of a patient.

As previously discussed, body 32 of diffuser 4 has a contoured inner surface, forming a somewhat triangular cup-shape which follows a shape of the nose/mouth nexus of a patient, thereby forming a shape plume of oxygen-enriched air in front of the patient's face. The enclosed volume of that cup may be modified to accommodate a larger plume and increase the total oxygen delivered during respiratory inspiration. As can be seen in FIG. 3, the wall 48 of body 32 near outer rim 38 becomes more aligned with the flow of oxygen out of outlet 38, with opposite sides becoming parallel. This shaping of the wall of diffuser 4 permits a concentrating of oxygen and a shaping of the plume, providing a more precise direction of the plume of oxygen-enriched air towards a patient's nose/mouth. The body 32 of diffuser 4 swivels about the corresponding end of elbow 28 to enable proper orientation of the diffuser when the diffuser is in different positions on a user's head, as illustrated in FIGS. 1 and 4.

Support 2 is optionally, but preferably, also provided with a securing means 50 for a carbon dioxide monitor intake 52. In prior oxygen diffuser systems, such as that described in applicant's corresponding U.S. application Ser. No. 10/186, 015, the intake for carbon dioxide monitoring was located within the body of the diffuser itself. It has been found that high oxygen flow rate through the diffuser has made the accuracy of the carbon dioxide monitoring through such a centrally positioned intake to be less than that which would have been desirable. Accordingly, in accordance with the present invention, the carbon dioxide intake 52 is intentionally spaced from the diffuser for itself. Inlet 52 is similarly held in a flexible plastic tube 54 with an embedded wire 56 which permits positioning of inlet 52 as desired, proximal to the patient's nose or mouth, when support 2 is in position on the patient. Carbon dioxide inlet 52 can be suitably positioned to receive exhaled air (carbon dioxide) from a patient's nose or mouth. The other end of tube 54 in operation is appropriately connected to a tube leading to an appropriate carbon dioxide monitor device (not illustrated).

It will be understood that the diffuser support of the present invention enables comfortable but secure positioning of the oxygen diffuser 4 and/or carbon dioxide monitor inlet 52 at alternative positions on a patient's head, as may be dictated by the patient's condition and the medical treatment being applied to that patient. The support when mounted on a patient's head, provides the necessary stability and security to minimize unintentional displacement of the support and its associated diffuser and carbon dioxide monitor inlet, by a patient.

As well, the support according to the present invention provides an easy avenue to aerosolize medication to a patient by introduction of an aerosol of that medication downstream, along, or before, oxygen delivery tube 8.

Thus, it is apparent that there has been provided in accordance with the invention a support for a lightweight oxygen diffuser that fully satisfies the objects, aims and advantages set forth above. While the invention has been described in conjunction with illustrated an embodiment thereof, it is evident that many alternatives, modifications and variations will be apparent to those skilled in the art in light of the foregoing description. Accordingly, it is intended to embrace all such alternatives, modifications and variations as fall within the spirit and broad scope of the invention.

What is claimed is:

1. A lightweight oxygen delivery device for a patient comprising:
   (a) an elongated tube, the tube being bendable to a particular shape and capable of maintaining that shape, the tube to carry oxygen and having a first end and a second end, the first end to be releasably connectable to an oxygen delivery source;
   (b) a rigid elbow having a pair of ends and an oxygen delivery passageway extending between those ends, one of those ends being secured to the second end of the tube;
   (c) an oxygen diffuser connected to the other end of the elbow, the diffuser comprising a body having a wall, the interior surface of which wall is of generally concave configuration, circumscribing a centrally positioned oxygen outlet communicating with said other end of the elbow so as to receive oxygen from the elbow and direct the flow of oxygen delivered from the elbow generally towards the patient=s nose and mouth;
   (d) a baffle seated within the diffuser over the oxygen outlet, the baffle shaped and positioned so as to change oxygen flow from the diffuser from jet flow to turbulent flow;
   (e) a support for the diffuser, the support comprising a securing means for the elongated tube, the securing means being located at the vertex of front portions of rigid arms forming a v-shaped front of the support, a resilient front strap extending between rear portions of the arms and a resilient back strap extending between ends of the rear portions of the arm, in operation, the back strap arranged so as to extend behind a user's head and be releasably adjustable to an operative length to seat the support securely on a user's head with a portion of the front of the user's face bearing against the front strap, so that, when so seated, the diffuser is held in a position spaced from proximal to the patient's nose and mouth.

2. A device according to claim 1, wherein the securing means and front portions and rear portions of the arms are of integral construction.

3. A device according to claim 1, wherein one end of the back strap is anchored to a corresponding arm, and another end of the strap is slidable and releasably securable within a keyway aperture in the end of the other arm to permit adjustment of the operative length of the back strap.

4. A device according to claim 1, wherein the elongated tube is a flexible tube within which a wire is embedded to permit bending of the tube to a particular shape and maintaining of that shape.

5. A device according to claim 1 further comprising a means positioned on an arm of the support for securing an intake for a carbon dioxide monitor, and an intake for a carbon dioxide monitor is secured to said means.

6. A device according to claim 1, wherein the straps are of rubber.

7. A device according to claim 1, wherein the diffuser wall is of cup-shaped appearance, extending from a base where the oxygen outlet is positioned, outwardly and upwardly to an edge of triangular peripheral contour.

8. A device according to claim 7, wherein the corners of the edge are rounded and one of the corners, intended when in use to be the uppermost corner, and portions of the wall edge proximal to said one of the corners, are slightly raised with respect to the other corners and edge portions, to facilitate direction of oxygen towards a patient's nose and mouth.

9. A device according to claim 8, wherein the baffle comprises a post centrally positioned in the diffuser body and upwardly extending from the oxygen outlet, the post terminating in a cap having sides downwardly and outwardly extending towards the oxygen outlet.

10. A device according to claim 5, wherein the diffuser wall is of cup-shaped appearance, extending from a base where the oxygen outlet is positioned, outwardly and upwardly to an edge of triangular peripheral contour.

11. A device according to claim 9, wherein the corners of the edge are rounded and one of the corners, intended when in use to be the uppermost corner, and portions of the wall edge proximal to said one of the corners, are slightly raised with respect to the other corners and edge portions, to facilitate direction of oxygen towards a patient's nose and mouth.

12. A device according to claim 1, wherein the diffuser is provided with a swivel attachment to the elbow whereby the diffuser may be rotated 360° on the elbow.

13. A device according to claim 4, wherein the carbon dioxide monitor tube is flexible and a wire is embedded therein to permit bending of the tube to a particular shape and maintaining of that shape.

14. A device according to claim 1, wherein the securing means comprises a sleeve for securing the elongated tube.

15. A support for an oxygen diffuser for delivering a plume of oxygen-enriched air to a space in front of a patient's nose and mouth, the support comprising a means for holding a tube associated with the oxygen diffuser, said means located at the vertex of front portions of rigid arms forming a v-shaped front of the support, a resilient front strap extending between rear portions of the arms, a resilient back strap extending between ends of the rear portions of the arms, in operation, the back strap arranged so as to extend behind a user's head and be releasably adjustable to an operative length to seat the support securely on a user's head with a portion of the front of the user's face bearing against the front strap, so that, when so seated, the diffuser is held in a position spaced from but proximal to the patient's nose and mouth.

16. A support according to claim 15, wherein the means for holding the tube is a sleeve.

17. A support according to claim 16, wherein the sleeve and front portions and rear portions of the arms are of integral construction.

18. A support according to claim 15, wherein one end of the back strap is anchored to the corresponding arm, and another end of the back strap is slidable and releasably securable within a keyway aperture in the end of the other arm, to permit adjustment of the operative length of the back strap.

19. A support according to claim 15 comprising a means on an arm of the support for securing an intake for a carbon dioxide monitor.

20. A support according to claim 15, wherein the straps are of rubber.

* * * * *